United States Patent
Lester et al.

(10) Patent No.: US 6,626,947 B2
(45) Date of Patent: Sep. 30, 2003

(54) PRESS FIT ACETABULAR CUP AND ASSOCIATED METHOD FOR SECURING THE CUP TO AN ACETABULUM

(75) Inventors: Mark B. Lester, Warsaw, IN (US); Michael C. Jones, North Webster, IN (US); James C. Kudrna, Lakeforest, IL (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/858,411

(22) Filed: May 16, 2001

(65) Prior Publication Data

US 2002/0040245 A1 Apr. 4, 2002

Related U.S. Application Data

(63) Continuation-in-part of application No. 09/678,032, filed on Oct. 3, 2000.

(51) Int. Cl.$^7$ .................................................. A61F 2/32
(52) U.S. Cl. ................. 623/22.23; 623/22.12; 623/902
(58) Field of Search .................. 623/22.11–22.12, 623/22.21, 22.23, 22.24, 22.32, 22.34, 22.36, 22.38, 902; 606/79–81, 86, 91

(56) References Cited

U.S. PATENT DOCUMENTS

| | | | |
|---|---|---|---|
| 4,695,282 A | | 9/1987 | Forte et al. |
| 4,704,127 A | | 11/1987 | Averill et al. |
| 4,892,549 A | * | 1/1990 | Figgie et al. ............ 623/22.23 |
| 5,030,402 A | | 7/1991 | Zachariades |
| 5,098,434 A | * | 3/1992 | Serbousek ................ 606/66 |
| 5,782,928 A | * | 7/1998 | Ries et al. ............... 623/22.21 |
| 5,935,174 A | | 8/1999 | Dye |
| 5,938,702 A | | 8/1999 | Lopez et al. |
| 5,972,032 A | | 10/1999 | Lopez et al. |
| 6,017,975 A | | 1/2000 | Saum et al. |
| 6,027,503 A | * | 2/2000 | Khalili et al. ................ 606/81 |
| 6,059,830 A | * | 5/2000 | Lippincott et al. ........ 623/18.11 |
| 6,132,469 A | * | 10/2000 | Schroeder .................... 606/99 |
| 6,245,276 B1 | | 6/2001 | McNulty et al. |
| 6,416,553 B1 | * | 7/2002 | White et al. ............ 623/22.38 |

FOREIGN PATENT DOCUMENTS

| | | |
|---|---|---|
| EP | 0722973 | 7/1996 |
| EP | 0729981 | 9/1996 |
| WO | WO 99/52474 | 10/1999 |

OTHER PUBLICATIONS

Dijkstra, D.J. et al., "Cross–linking of ultra–high molecular weight polyethylene in the melt by means of electron beam irradiation", Polymer, Jordan Hill, Oxford, Great Britain, vol. 30, No. 5, May 1, 1989, pp. 866–873.

* cited by examiner

Primary Examiner—David J. Isabella
Assistant Examiner—Urmi Chattopadhyay
(74) Attorney, Agent, or Firm—Maginot, Moore & Bowman

(57) ABSTRACT

An acetabular cup and method of securing the acetabular cup to an acetabulum so as to provide a bearing surface for a head portion of a femur is provided. The acetabular cup is shaped to provide a cementless, press-fit into a reamed acetabulum. The acetabular cup is formed of a body having a sidewall defining a radius from a center point of the annular rim to the sidewall wherein the radius increases in length from the apex to said annular rim. The method of securing the acetabular cup first includes reaming the acetabulum with a reamer having a head with a radius of curvature that is less than the radius from the center point to the annular rim of the acetabular cup.

15 Claims, 7 Drawing Sheets

PRESS FIT ACETABULAR CUP AND ASSOCIATED METHOD FOR SECURING THE CUP TO AN ACETABULUM

This application is a continuation-in-part and claims the benefit of co-pending U.S. patent application Ser. No. 09/678,032 filed Oct. 3, 2000 entitled Press Fit Acetabular Cup and Associated Method For Securing the Cup to an Acetabulum.

TECHNICAL FIELD OF THE INVENTION

The present invention relates generally to an acetabular cup and, more particularly, to a press-fit acetabular cup and associated method for securing the cup to an acetabulum.

BACKGROUND OF THE INVENTION

During the lifetime of a patient, it may be necessary to perform a hip replacement procedure on the patient as a result of, for example, disease or trauma. The hip replacement procedure may involve a total hip replacement or a partial hip replacement. In a total hip replacement procedure, a femoral component having a head portion is utilized to replace the natural head portion of the thighbone or femur. The femoral component typically has an elongated intramedullary stem which is utilized to secure the femoral component to the patient's femur. In such a total hip replacement procedure, the natural bearing surface of the acetabulum is resurfaced or otherwise replaced with a cup-shaped acetabular component that provides a bearing surface for the head portion of the femoral component.

Acetabular cups may be secured to the acetabulum in a number of different manners. For example, acetabular cups may be secured to the acetabulum by the use of bone cement. However, recent studies have speculated that it may be desirable to secure artificial components to natural bone structures without the use of bone cement. Hence, a number of press fit acetabular cups have been designed for securement to the acetabulum without the use of bone cement.

In either case (i.e. cemented or cementless), the acetabulum is first reamed by the surgeon in order to create a cavity into which the acetabular cup is secured by the use of a surgical tool known as a reamer. It is often difficult for the surgeon to properly match the size of the reamer to the desired acetabular cup size.

Although press fit acetabular cups have heretofore been referred to as being "generally hemispherical" in shape, such heretofore-designed cups, in reality, are sub-hemispherical in shape. In particular, as shown in the prior art drawing of FIG. 7, a heretofore designed acetabular cup 100 has an apex or dome 102 at a proximal end 104 thereof along with an annular rim 106 at a distal end 108 thereof. In between the dome 102 and the annular rim 106, the prior art acetabular cup 100 has a sidewall that has a convex proximal surface and a concave distal surface.

However, as shown in FIG. 7, the configuration of the prior art acetabular cup 100 is sub-hemispherical. In particular, a "true" hemisphere 114 is shown in FIG. 7 as a phantom line overlay. As can be seen, a distal face 116 of the annular rim 106 does not, in fact, lie along the 180° surface (or loosely, the equator 118) of the hemisphere 114, but rather is recessed away from the equator 118 by a relatively significant distance X. In fact, it is not uncommon for prior art cup designs to be recessed from the equator 118 of the cup by as much as 4–5 millimeters (i.e. X=4–5 mm).

Such a configuration has a number of drawbacks associated therewith. For example, such a large recess distance X (i.e. 4–5 mm) renders it difficult for the surgeon to ream a properly sized cavity in the acetabulum. In particular, the cutting head of heretofore-designed reamers are typically configured as relatively true hemispheres. Hence, when a surgeon reams the patient's acetabulum, the surgeon has to "estimate" the approximate depth of the reamed recess. More specifically, if the surgeon reams all the way to the 180° surface or "equator" of the reamer, the annular rim 106 of the acetabular cup 100 will be recessed in the reamed cavity. Conversely, if the surgeon does not ream deeply enough (i.e. "under reams"), the acetabular cup 100 will not be fully seated in the reamed cavity of the acetabulum. In light of the fact that surgeons occasionally select a reamer that is slightly smaller in size than the acetabular cup to be implanted, under reaming may also disadvantageously lead to bone fracture of the acetabulum since excessive force is often utilized to insert the cup into the undersized (i.e. under reamed) cavity. Some of the early bone cemented cups did not suffer from this problem by being configured more closely as "true" hemispheres. However, as indicated above, such cups undesirably required the use of bone cement during implantation thereof.

Another drawback associated with heretofore-designed press fit acetabular cups relates to the configuration of the outer shell. In particular, in an attempt to increase retaining forces, a number of acetabular cups have been designed with a flared rim (known as dual radius or "bubble" cups) or a frusto-conically shaped annular rim portion (known as dual-geometry cups). Although the configuration of such cups may generate relatively strong retention forces at the rim portion of the cup, surface contact and therefore retention forces are relatively small at the portions of the outer shell other than the rim portion, particularly in the dome area. Moreover, such reduced surface contact at the portions of the outer shell other than the rim portion reduces bone ingrowth in such portions.

With the above-mentioned heretofore-designed press-fit acetabular cups, a two-part reaming process is typically necessary. The two-part reaming process involves reaming of the acetabulum using a reamer of a first size, then reaming the acetabulum using a reamer of a second size. The more reaming, the more likely that a problem will occur. For example, many conventional cementless acetabular cup systems use a cup that is two millimeters (2 mm) larger than the last reamer size used. Inserting this size cup into the under-sized reamed acetabulum to accommodate this system is sometimes difficult, particularly with resistance in the dome area of the cup, which is also larger than the last reamer size used.

What is needed therefore is an acetabular cup and associated method that overcomes one or more of the above-mentioned drawbacks.

What is further needed is an acetabular cup and associated implant method that allows for the cup to be secured to the acetabulum without the use of bone cement.

What is also needed is an acetabular cup and associated implant method that facilitates greater amounts of bone ingrowth relative to heretofore designed acetabular cups.

What is still further needed is a cementless acetabular cup that utilizes a single reaming process for implant.

SUMMARY OF THE INVENTION

The present invention is a press-fit acetabular cup and method of securing the acetabular cup to an acetabulum so as to provide a bearing surface for a head portion of a femur. The acetabular cup is shaped to provide a cementless, press-fit into a reamed acetabulum. The acetabular cup is formed of a body having a sidewall defining a radius from a center point of the annular rim to the sidewall wherein the radius increases in length from the apex to said annular rim. The method of securing the acetabular cup first includes reaming the acetabulum with a reamer having a head with a radius of curvature that is less than the radius from the center point to the annular rim of the acetabular cup.

According to one embodiment of the present invention, there is provided an acetabular cup. The acetabular cup includes a body defining a dome having an apex and an annular rim. The dome is defined by an increasing radius sidewall that extends from the apex to the annular rim. The annular rim defines a plane having a center point. Wherein a radius from the center point to the annular rim has a first given length, 1L, the center point to the apex defining a second given length, 2L, and the second given length is less than the first given length.

According to another embodiment of the present invention there is provided an acetabular cup. The acetabular cup includes a dome-shaped shell having an apex and an annular rim. The dome-shaped shell has a sidewall defining a radius from a center point of the annular rim to the sidewall, wherein the radius increases in length from the apex to the annular rim.

According to yet another embodiment of the present invention, there is provided a method of securing an acetabular cup to an acetabulum. The method includes reaming a cavity of a first radius of curvature into an acetabulum with a reamer, the reamer including a reamer head having the first radius of curvature, and press fitting an acetabular cup into the reamed cavity, the acetabular cup having a body defining a dome having an apex and an annular rim, the dome defined by a gradually increasing radius sidewall that extends from the apex to the annular rim, the annular rim defining a plane having a center point, wherein a radius from the center point to the annular rim has a first given length, 1L, the center point to the apex defining a second given length, 2L, the second given length is less than the first given length, the first given length is greater than the first radius of curvature, and the second given length is approximately equal to the first radius of curvature.

According to a further embodiment of the present invention, there is provided a method of securing an acetabular cup to an acetabulum. The method includes reaming a cavity of a first radius of curvature into an acetabulum with a reamer, the reamer including a reamer head having the first radius of curvature, and press fitting an acetabular cup into the reamed cavity, the acetabular cup having a dome-shaped shell having an apex and an annular rim, the dome-shaped shell having a sidewall defining a shell radius from a center point of the annular rim to the sidewall, wherein the shell radius gradually increases in length from the apex to the annular rim, and the shell radius at the annular rim is greater than the radius of curvature.

The present cementless acetabular cup provides an enhanced peripheral press-fit with reduced loading in the dome area. This helps provide initial stability for bone ingrowth and long-term fixation. Further, a good peripheral fit may help protect against the migration of wear debris from a "pumping action" of the effective joint space.

Additionally, reamer to cup dimensions of the present acetabular cup have a line-to-line fit in the dome area with a gradual increase in press-fit or size from the dome to the rim. This allows the present acetabular cup to achieve maximization of peripheral contact for stability while minimizing dome loading and helping reduce the risk of acetabular fracture.

The present acetabular cup also accepts a polyethylene liner or insert such that the cup and liner achieve congruency therebetween without rim loading the liner. A positive locking mechanism and anti-rotation devices in the metal shell/body defining the acetabular cup secure the liner to the shell. Congruency and secure locking of the polyethylene liner work together to reduce micromotion at the shell/liner interface. Further, such high conformance between the shell and the liner results in efficient load transfer and reduce contact stresses.

BRIEF DESCRIPTION OF THE DRAWINGS

The various objects, features, and advantages of the present invention will become apparent and/or better understood by reference to the following descriptions of the embodiments of the present invention taken in conjunction with the accompanying drawing wherein.

DETAILED DESCRIPTION OF THE INVENTION

Figure 1:
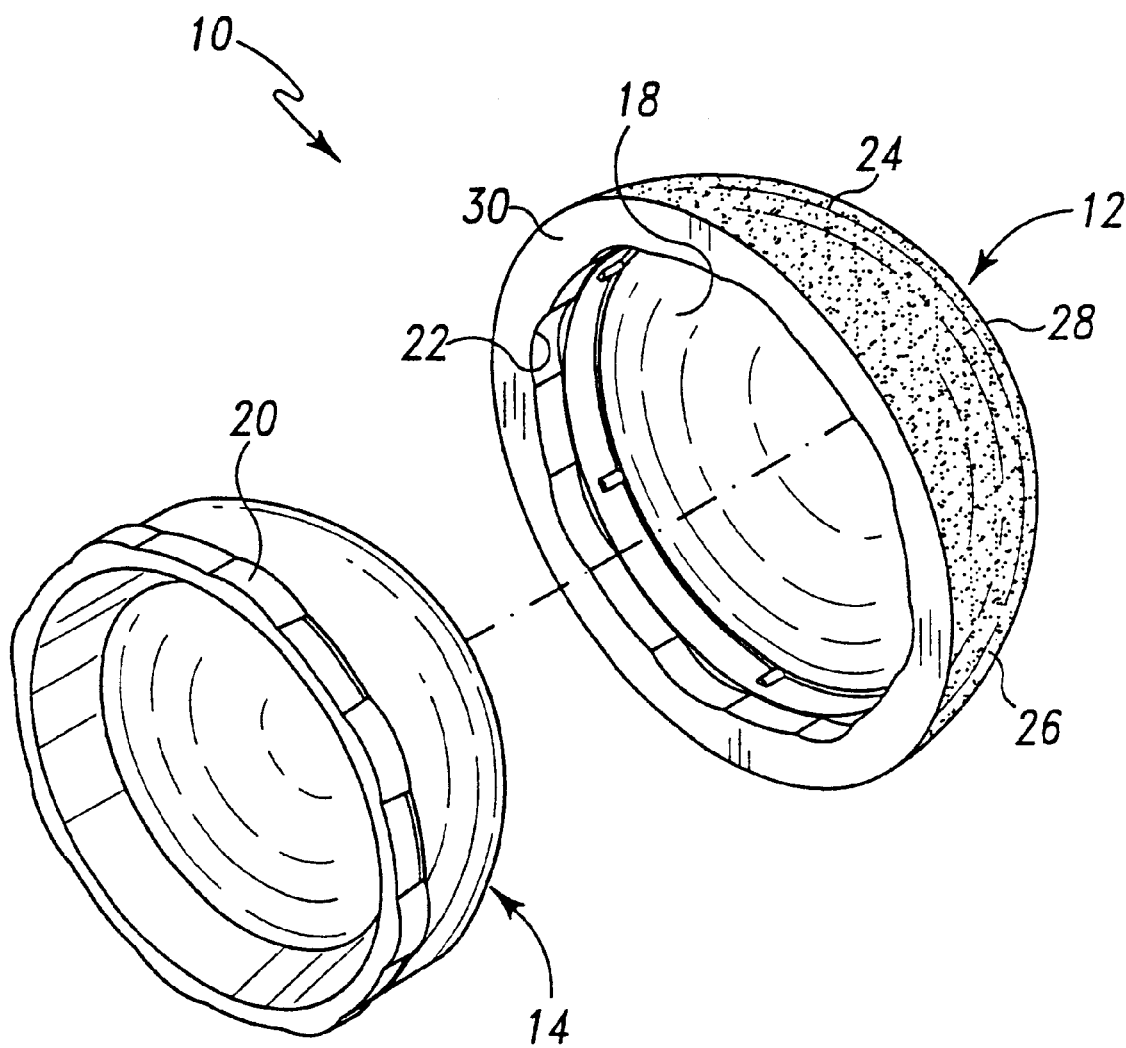
FIG. 1 is an exploded perspective view that shows an acetabular cup and associated bearing insert that incorporate the features of the present invention therein.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Referring now to FIG. 1, there is shown a prosthetic hip assembly 10 for use in either a partial or total hip replacement procedure. The prosthetic hip assembly 10 includes an acetabular component or cup 12 and a bearing insert 14. Collectively, the acetabular cup 12 and the bearing insert 14 provide an artificial bearing surface on which a natural or artificial head portion of a femur (not shown) may bear. In particular, as shall be discussed in greater detail, the acetabular cup 12 is implanted into a patient's acetabulum 16 (see FIGS. 4 and 5) such that the bearing insert 14 may then be positioned in an insert-receiving cavity 18 (see FIG. 1) defined in the acetabular cup 12. The bearing insert 14 is preferably constructed from a polymeric material such as polyethylene or ultra-high molecular weight polypropylene (UHMWPE) thereby providing a desirable artificial surface on which the head portion of the femur may bear.

As shown in FIG. 1, the bearing insert 14 has a number of keying tabs 20 defined therein. The keying tabs 20 are received into a number of corresponding keying slots 22 defined in the acetabular cup 12 to prevent rotation of the bearing insert 14 relative to the acetabular cup 12 when the bearing insert 14 is positioned in the insert-receiving cavity 18 of the cup 12.

Figure 2:
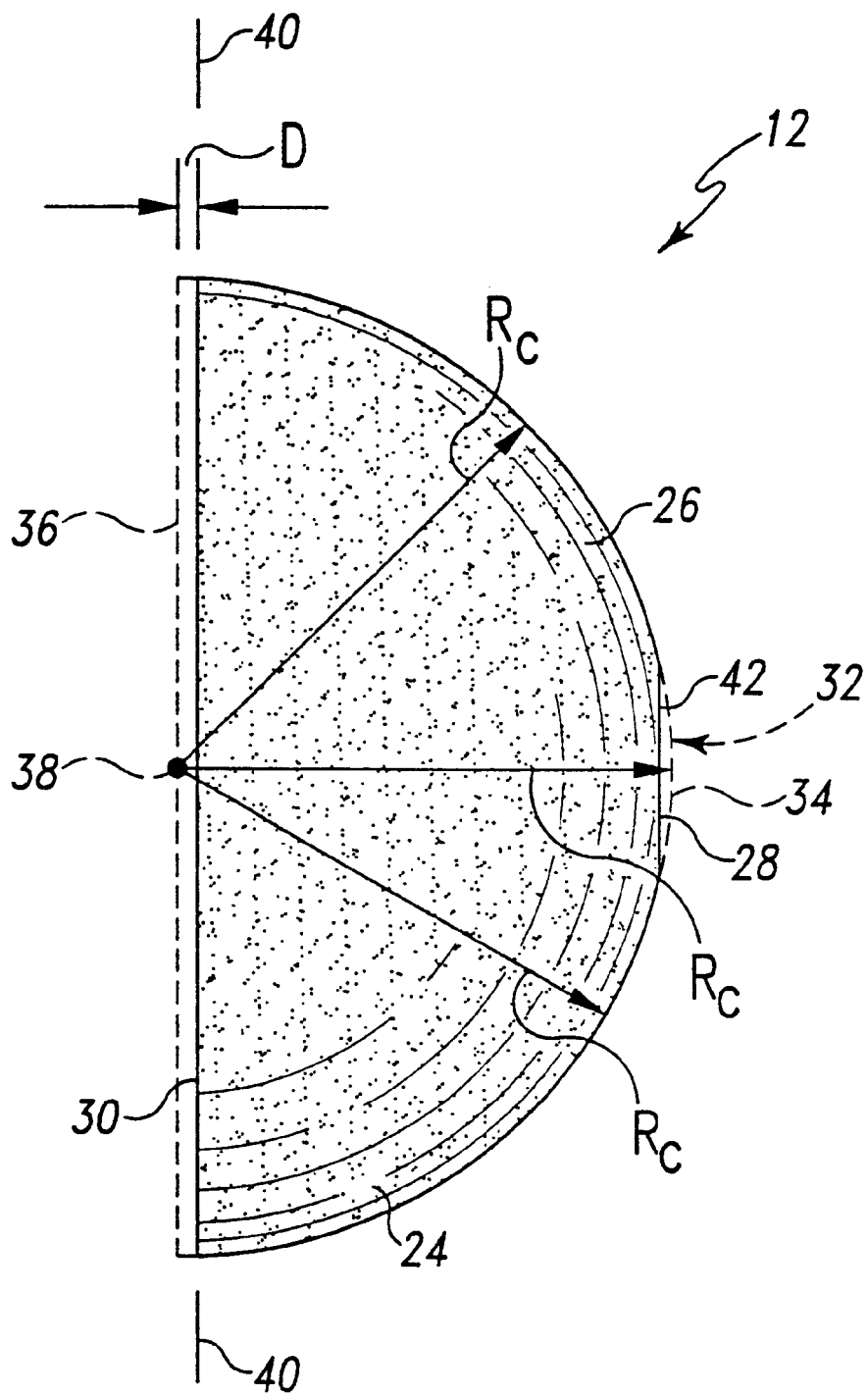
FIG. 2 is an enlarged side elevational view of the acetabular cup of FIG. 1 with an imaginary true hemisphere superimposed thereon.

As shown in FIGS. 1 and 2, the acetabular cup 12 includes a cup body or shell 24 that has a sidewall 26. The body 24 may be made of any suitable material such as a titanium alloy. One such titanium alloy is Ti-6Al-4V. The sidewall 26 has a textured or porous outer surface. Such a textured or porous outer surface enhances bone ingrowth thereby facilitating long-term attachment of the acetabular cup 12 to the acetabulum 16. Such a textured or porous outer surface may be a POROCOAT® porous coating may be DePuy Orthopaedics of Warsaw, Ind.

The sidewall 26 extends outwardly at a substantially constant radius $R_C$ from an apex or dome 28 of the body 24 to an annular rim 30. In particular, as shown in FIG. 2, an imaginary hemisphere 32 may be superimposed over the acetabular cup 12. The imaginary hemisphere 32, as with any true hemisphere, possesses an apex 34 and a great circle 36. The great circle 36 is the circle that is defined by the intersection of the surface of a sphere by a plane that passes through the center of the sphere. In essence, a sphere that is bisected along its "equator" into two equal halves forms a great circle at the plane of bisection. Hence, the center point of the bisected sphere is the center point of the great circle of the hemisphere. Accordingly, every point along the surface of the imaginary hemisphere 32 (and hence every point on the outer surface of the sidewall 26) lies an equal distance (i.e. the radius $R_C$) from a center point 38 of the great circle 36 of the imaginary hemisphere 32. Indeed, substantially every point on the sidewall 26 of the cup body 24 is positioned a distance that is equal to the radius $R_C$ away from the center point 38 of the great circle 36. It should be appreciated that the textured or porous outer surface of the sidewall 26 creates a somewhat irregular or "jagged" outer surface. Hence, as used herein, the term "sidewall", when utilized in the context of "every point on the sidewall being positioned a distance equal to the radius (i.e. $R_C$) away from the center point of the great circle", is intended to mean the average or mean height of the jagged outer surface of the sidewall thereby factoring out any slight fluctuations in the distance from the center point of the great circle caused by the textured or porous outer surface of the sidewall.

The outer face of the annular rim 30 of the cup body 24 defines a segmental plane 40 (shown as a line in the side elevational view of FIG. 2) that intersects the imaginary hemisphere 32. The segmental plane 40 is oriented substantially parallel to the great circle 36 and is spaced apart from the great circle 36 by a relatively small distance D. Hence, every point on the outer peripheral edge of the annular rim is spaced apart from the great circle 36 by the distance D. In one exemplary embodiment, distance D is between 0.5 and 2.0 millimeters. In a more specific embodiment, distance D is approximately 1 millimeter.

As a result, the cup body 24 of the acetabular cup 12 is configured as a substantially true hemisphere. Indeed, with the exception of (1) the portion of the cup 12 near its apex 28 which is removed in order to facilitate a threaded aperture 42 which is utilized during implantation of the cup 12, and (2) the portion of the sidewall 26 which would be present if the sidewall 26 was extended the distance D toward the great circle 32 of the imaginary hemisphere 32, the cup body 24 is, in fact, configured as a true hemisphere. As shall be discussed below, such a configuration (i.e. that of a nearly true hemisphere) provides numerous advantages to the acetabular cup 12 relative to heretofore-designed cups.

Figure 3:
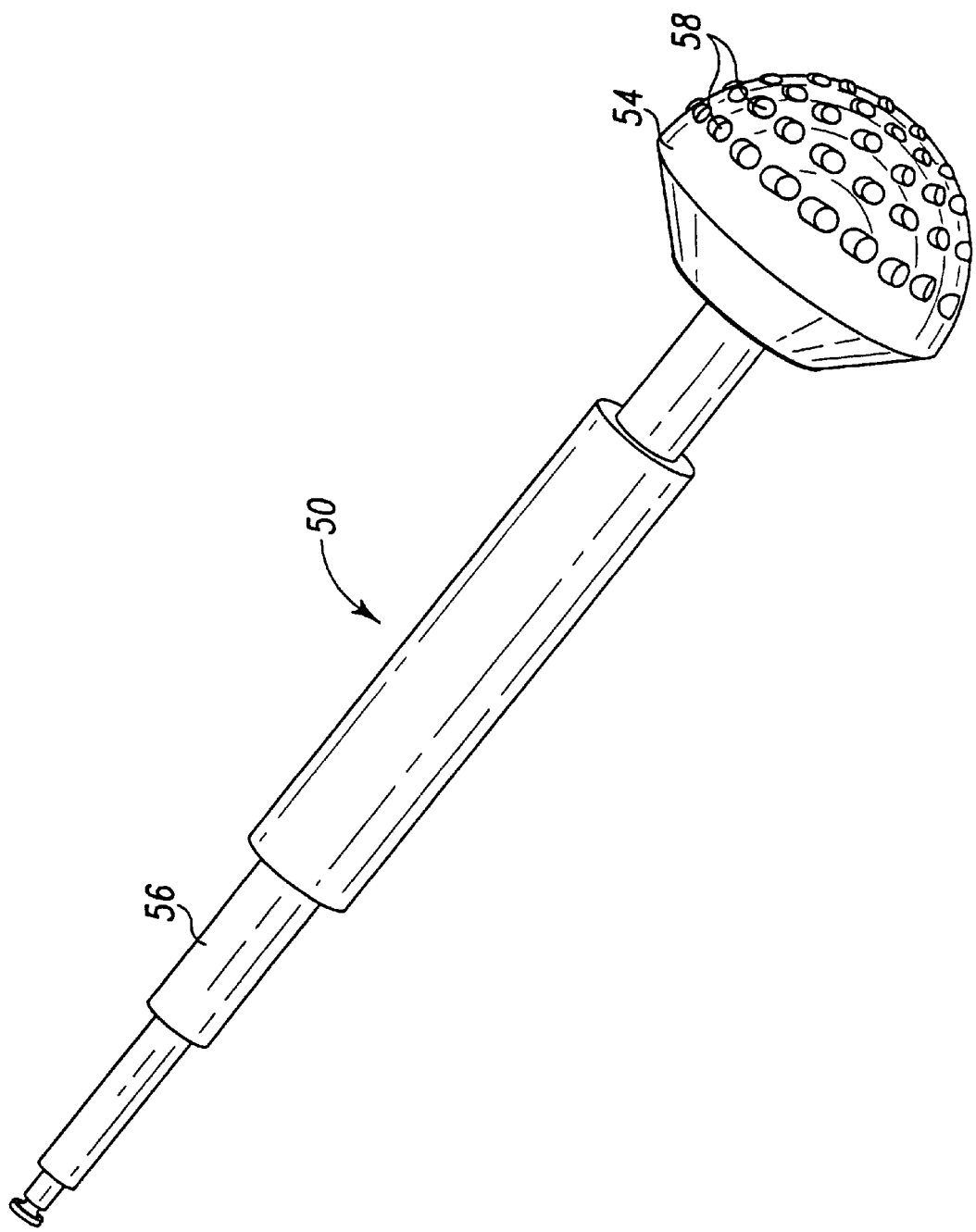
FIG. 3 is a perspective view of a reamer that is utilized to ream the acetabulum of a patient prior to implantation of the acetabular cup of FIG. 1.

Referring now to FIG. 3, there is shown a cutting tool or reamer 50 associated with the prosthetic hip assembly 10. The reamer 50 is utilized to ream or otherwise cut the acetabulum 16 in order to form a hemispherically shaped cavity 52 therein (see FIG. 4). The reamer 50 includes a cutting head 54 secured to a shaft 56. The cutting head 54 includes a number of cutting projections 58 which are configured to engage and remove bone material from the patient's acetabulum 16. The outer edges of the cutting projections 58 define the radius of the hemispherically shaped cutting head 54. In one exemplary embodiment, the cutting projections 58 of the cutting head 54 define a true hemisphere. In particular, the general profile created by the cutting projections 58 (and hence the cavity created by the reamer 50) is that of a true hemisphere.

Moreover, the radius of the cutting head 54 is preferably slightly smaller than the radius $R_C$ of the acetabular cup 12. In one exemplary embodiment of the present invention, the radius of the cutting head 54 is between one-half (0.5) and one and one-half (1.5) millimeters smaller than the radius $R_C$ of the acetabular cup 12. In a more specific exemplary embodiment of the present invention, the radius of the cutting head 54 is approximately one (1) millimeter smaller than the radius $R_C$ of the acetabular cup 12. For example, if the anatomy of a given patient requires the use of a fifty-six millimeter acetabular cup 12 (i.e. an acetabular cup having an outer diameter of 56 mm), the reamer 50 utilized to ream the patient's acetabulum 16 preferably has a cutting head diameter of fifty-four millimeters (i.e. the outer diameter of the cutting head is 54 mm). Such use of a smaller reamer 50 provides numerous advantages. For example, it has been found that such use of a slightly smaller reamer 50 creates a cavity 52 in the acetabulum 16 which provides preferable amounts of insertion resistance thereby firmly retaining the acetabular cup 12 upon press fit thereof into the cavity 52 without requiring insertion forces large enough to crack or otherwise break the acetabulum.

Figure 4:
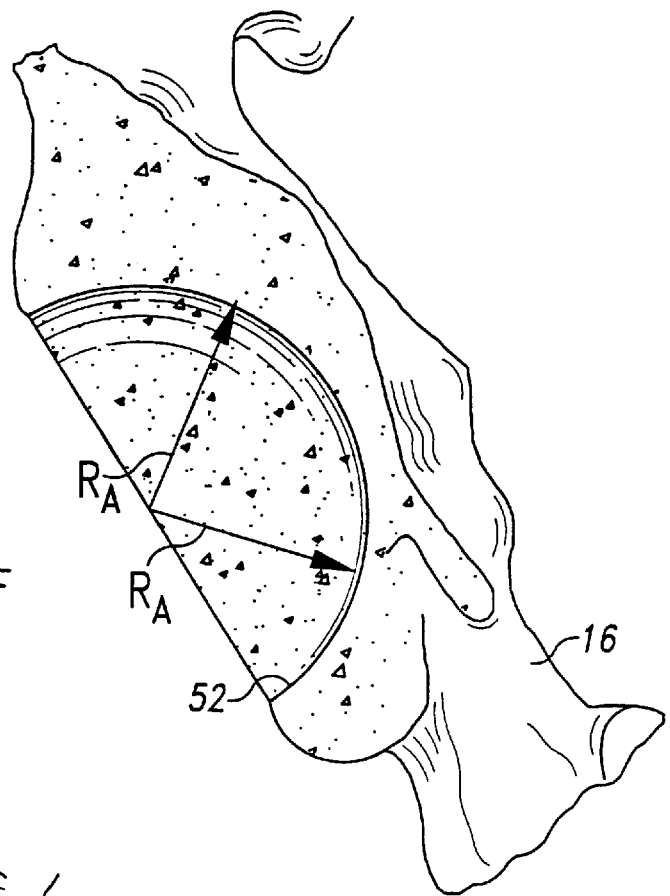
FIG. 4 is a perspective view of the acetabulum subsequent to reaming with the reamer of FIG. 3.
Figure 5:
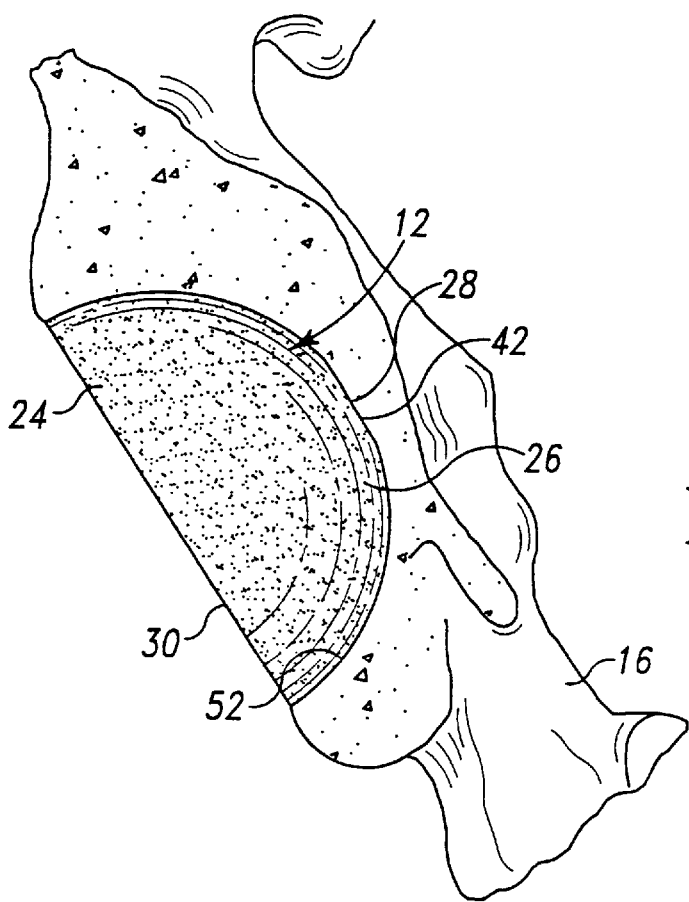
FIG. 5 is a view similar to FIG. 4, but showing the acetabular cup press fit into the cavity reamed into the acetabulum by the reamer.

Hence, as shown in FIG. 4, use of the reamer 50 to ream the acetabulum produces the cavity 52 having a radius $R_A$. As described above, the radius of the cutting head 54 of the reamer 50 is preferably slightly smaller than the radius $R_C$ of the acetabular cup 12. Hence, the radius $R_A$ reamed into the cavity 52 of the acetabulum 16 is likewise slightly smaller than the radius $R_C$ of the acetabular cup 12. Such a slight difference in radius size provides for enhanced implantation properties. In particular, as alluded to above, the acetabular cup 12 is configured to be press fit into the reamed cavity 52 of the acetabulum 16 without the use of bone cement. As such, the nearly true hemispheric shape of the acetabular cup 12 provides for constant contact with the reamed hemispherically shaped cavity 52 of the acetabulum 16 along the entire outer surface of the cup body 24.

Moreover, the presence of a slightly smaller radius $R_A$ of the cavity 52 also causes a need for a slight increase in the insertion force (i.e. the press fit) as the cup 12 is implanted in the direction from the dome 28 to the annular rim 30. This slightly increased resistance enhances the retention of the cup 12 when it is press fit into the acetabulum 16. In addition, since the cavity 52 is reamed, for example, two (2) millimeters smaller in diameter relative to the acetabular cup 12 (i.e. $R_A$ is 2 mm smaller than $R_C$), an approximately one millimeter difference is created on each "side" of the annular rim 30.

Figure 6:
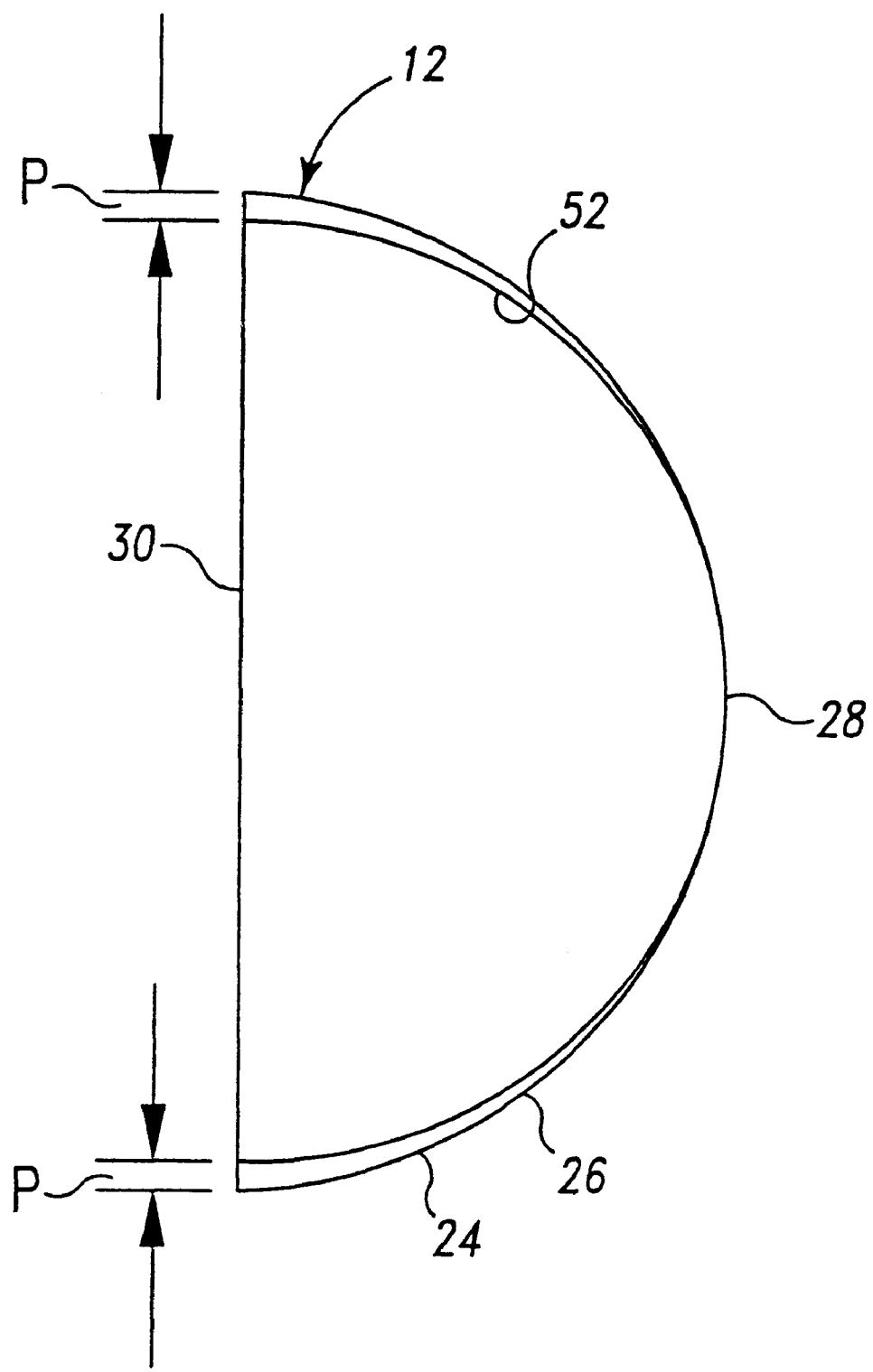
FIG. 6 is a diagrammatic view that shows an outline of the acetabular cup of FIG. 1 superimposed on an outline of the cavity reamed into the acetabulum by the reamer.

Indeed, as shown in FIG. 6 according to one aspect thereof, a "graduated" or slightly increasing press fit is created as the acetabular cup 12 is implanted into the acetabulum 16. Specifically, line-to-line contact exists between the cup 12 and the cavity 52 in the area near the dome 28 of the cup 12. Hence, the press fit of the cup 12 into the cavity 52 gradually increases from approximately zero in the areas of such line-to-line contact (i.e. the dome 28) to a press fit that equals a distance P on each "side" of the cup 12 at the annular rim 30. In an exemplary case, the distance P is one millimeter (1 mm) thereby creating an overall press fit of two millimeters (2 mm) at the annular rim 30 of the cup 12. This increasing press fit provides for a reliable (i.e. stable) press fit of the acetabular cup 12 into the reamed cavity 52 thereby further enhancing the retention of the cup 12 in the reamed cavity 52.

Moreover, as described above, since both the reamed cavity 52 and the acetabular cup 12 are preferably configured as nearly true hemispheres having similar sizes, the outer surface of the sidewall 26 of the cup 12 contacts the reamed hemispherically shaped cavity 52 of the acetabulum 16 along substantially all of the surface of the cavity 52. Hence, the outer porous surface of the sidewall 26 of the acetabular cup 12 "scratches" or otherwise slightly abrades substantially all of the wall surface of the cavity 52 as the cup 12 is press fit into the cavity 52. This slight abrading facilitates bone ingrowth into the porous outer surface of the acetabular cup 12.

Figure 6A:
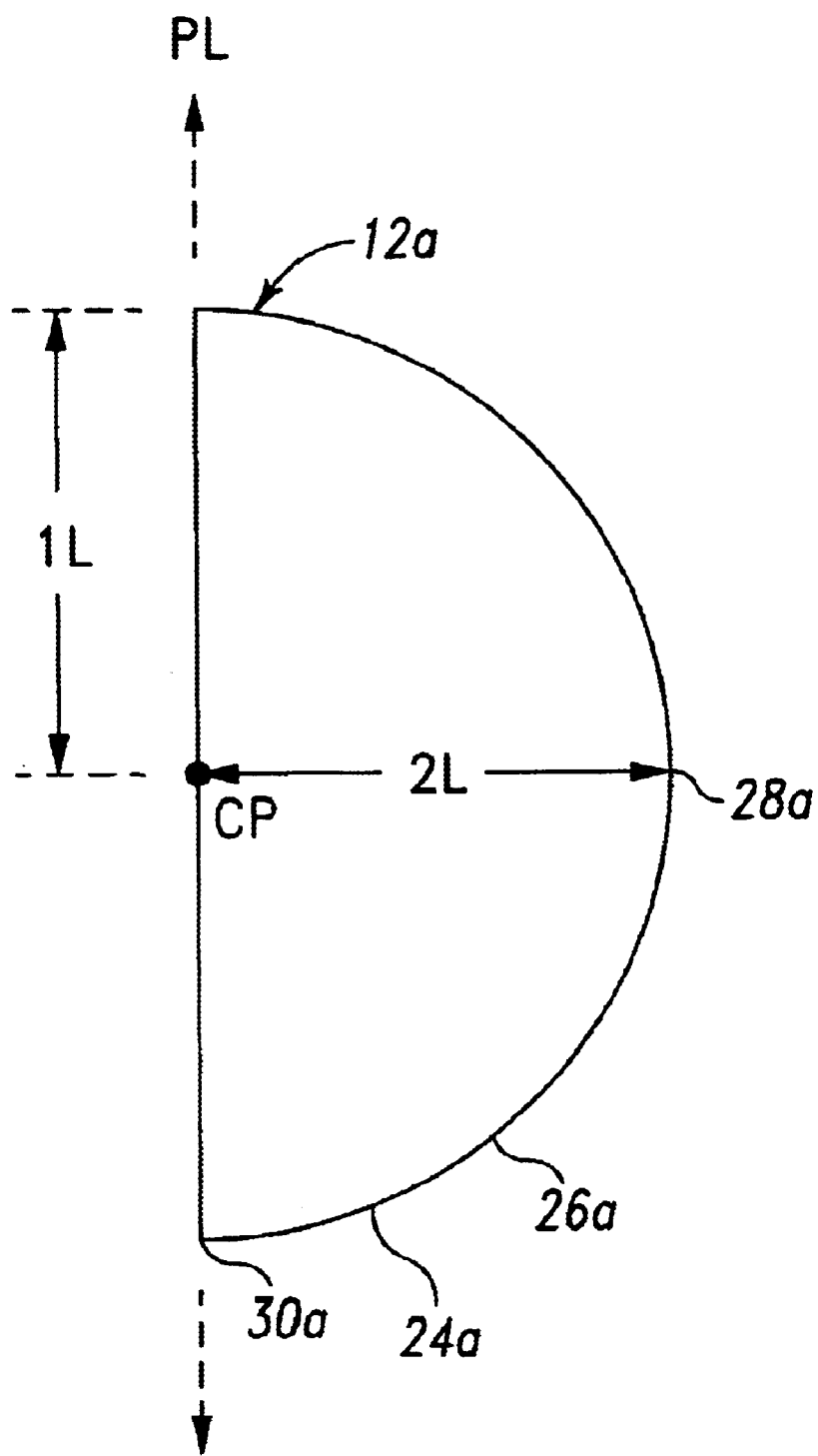
FIG. 6A is diagrammatic view that shows an alternative embodiment of an acetabular cup that may be utilized in the prosthetic hip assembly 10 of FIG. 1.
Figure 7:
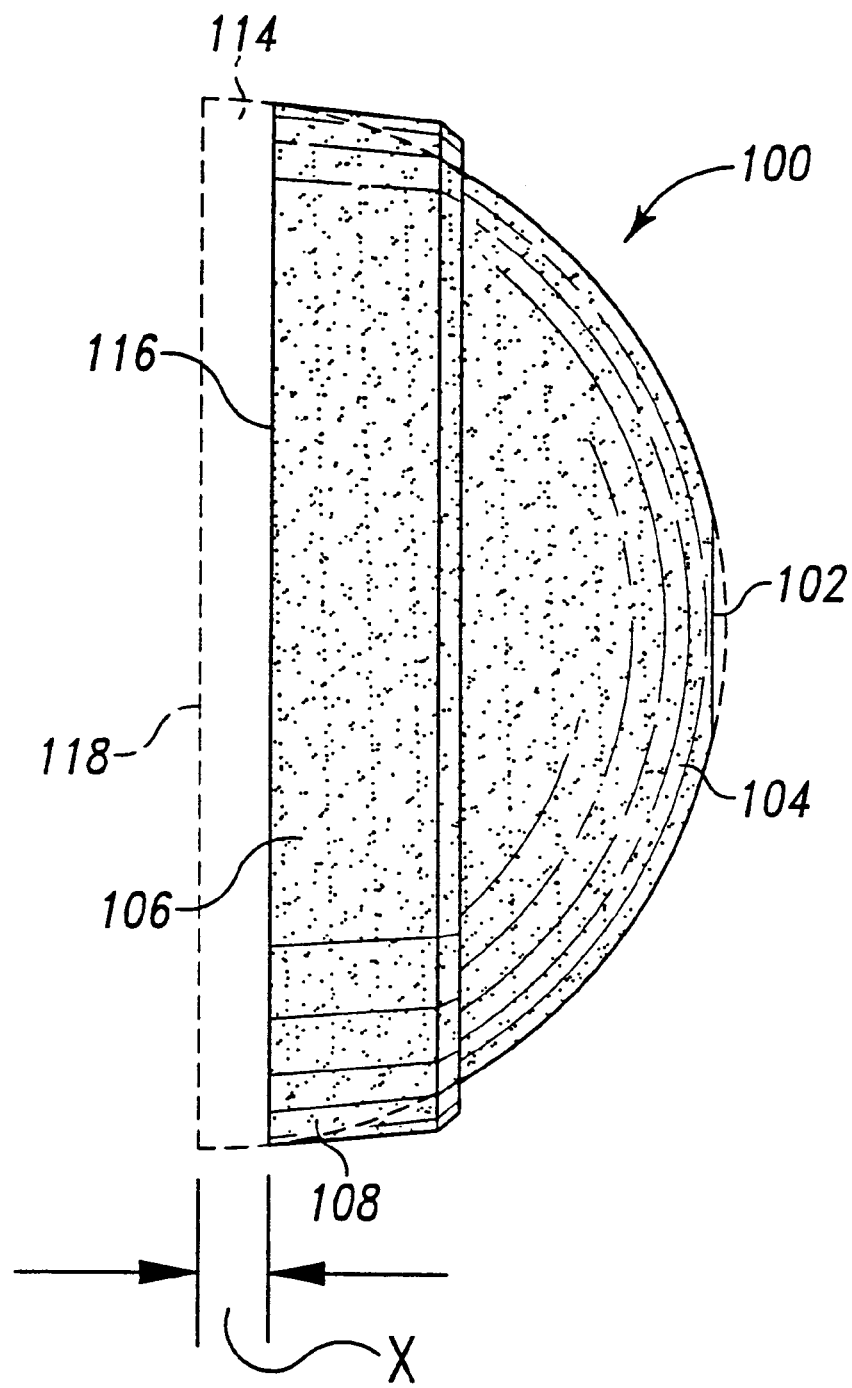
FIG. 7 is a side elevational view of a prior art acetabular cup.

As an alternative embodiment, the geometry of the acetabular cup 12 of the prosthetic hip assembly 10 of FIG. 1 may be modified as follows. In particular, a modified acetabular cup 12A is shown in FIG. 6A and is referred to by reference numeral 12A. The acetabular cup 12A has 24a a body defining a dome having an apex 28a, an annular rim 30a, and an outer sidewall 26a extending therebetween. The annular rim 30a defines a plane PL and has a center point CP lying in the plane. A radial distance between the center point CP and the sidewall 26a gradually increases from the apex 28a to the annular rim 30a. The radial distance from the center point CP to the annular rim 30a defines a first given length, 1L. Further, the radial distance from the center point CP to the apex 28a defines a second given length, 2L. Note that the second given length is less than the first given length. Further note that the first given length is greater than a radius of curvature of the cutting head 54 of the reamer 50 (see FIG. 3). Moreover, the second given length is approximately equal to the radius of curvature of the cutting head 54 of the reamer 50 (see FIG. 3). Preferably, 0.5 mm≦1L-2L≦2.0 mm. More preferably, 1L-2L is approximately 1.0 mm.

Operation of the Present Invention

In operation, the prosthetic hip assembly 10 of the present invention is utilized in the performance of either a total or partial hip replacement procedure in order to provide an artificial bearing surface for either a natural or artificial head portion of the femur without the use of bone cement. As shown in FIG. 4, the reamer 50 is first utilized to ream or otherwise cut the acetabulum 16 in order to form the hemispherically shaped cavity 52 therein. In particular, the surgeon rotates the reamer 50 such that the cutting projections 58 of the cutting head 54 engage and remove bone material from the patient's acetabulum 16. As described above, the radius of the cutting head 54 is preferably slightly smaller than the radius $R_C$ of the acetabular cup 12. For example, the reamer 50 utilized by the surgeon generally has a cutting radius that is approximately one (1) millimeter smaller than the radius $R_C$ of the acetabular cup 12 that is to be implanted. For example, if the anatomy of the patient requires the use of a fifty-six millimeter acetabular cup 12 (i.e. an acetabular cup having an outer diameter of 56 mm), the reamer 50 utilized to ream the patient's acetabulum 16 preferably has a cutting head diameter of fifty-four millimeters (i.e. the outer diameter of the cutting head is 54 mm).

Hence, as shown in FIG. 4, once the surgeon has utilized the reamer 50 to ream the acetabulum 16, the hemispherically shaped cavity 52 (having a radius $R_A$) is formed. Thereafter, the surgeon implants the acetabular cup 12 into the reamed acetabulum 16. In particular, the acetabular cup 12 is press fit into the reamed cavity 52 of the acetabulum 16 by the surgeon without the use of bone cement. During such press fitting, the true hemispherical shape of the acetabular cup 12 provides for constant contact with the reamed hemispherically shaped cavity 52 of the acetabulum 16 along the entire outer surface of the cup body 24. Moreover, the presence of a slightly smaller radius $R_A$ of the cavity 52 also causes a need for a slight increase in the insertion force as the cup 12 is implanted in the direction from the dome 28 to the annular rim 30. This increases the retention of the cup 12 when it is press fit into the acetabulum 16.

Moreover, since the cavity 52 is reamed, for example, two (2) millimeters smaller in diameter relative to the acetabular cup 12 (i.e. $R_A$ is 2 mm smaller than $R_C$), an approximately one millimeter difference is created on each "side" of the annular rim 30. This slight difference provides for a reliable (i.e. stable) press fit of the acetabular cup 12 into the reamed cavity 52.

In addition, during press fitting of the acetabular cup 12 into the reamed cavity 52, the outer porous surface of the sidewall 26 of the acetabular cup 12 "scratches" or otherwise slightly abrades substantially the entire wall surface of the cavity 52. As described above, this slight abrading facilitates bone ingrowth into the porous outer surface of the acetabular cup 12. Moreover, the similar configuration and size of the acetabular cup 12 and reamed cavity 52 allows the cup 12 to be fully seated into a position in which the annular rim 30 is substantially flush mounted with the distal surface of the acetabulum 16 (see FIG. 5) without requiring significant amounts of "estimating" by the surgeon during reaming of the bone.

Once the acetabular cup has been press fit into the cavity 52 defined in the acetabulum 16, the bearing insert 14 is installed. In particular, the bearing insert 14 may then be positioned in the insert-receiving cavity 18 (see FIG. 1) defined in the acetabular cup 12. As described above, the keying tabs 20 of the bearing insert 14 are received into the corresponding keying slots 22 defined in the acetabular cup 12 to prevent rotation of the bearing insert 14 relative to the acetabular cup 12. Once installed in such a manner, the bearing insert 14 provides a desirable artificial surface on which the artificial or natural head portion of the femur may bear.

Hence, as described herein, the prosthetic hip assembly 10 of the present invention provides numerous advantages over heretofore-designed assemblies. For example, the prosthetic hip assembly 10 of the present invention may be utilized to secure the acetabular cup to the acetabulum without the use of bone cement. Moreover, use of a constant radius, nearly true hemispherically-shaped acetabular cup provides for enhanced performance characteristics such as resistance to loosening and instability since the configuration of the cup distributes loads more evenly across the entire outer surface of the cup relative to heretofore designed dual-geometry or bubble cups. In addition, the use of a constant radius cup prevents the development of gaps near the flared outer rim surfaces of heretofore-designed dual-geometry or bubble cups. It is known that the presence of such gaps not only prevents bone ingrowth, but also undesirably facilitates the formation of lysis in the bone positioned near the rim of the cup.

In addition, since both the reamer 50 and the acetabular cup 12 are configured as nearly true hemispheres having similar sizes, the surgeon is not required to estimate the approximate depth as to when the acetabulum has been reamed deeply enough. This is a significant improvement over the use of heretofore-designed sub-hemispherical cups in which the surgeon must do such estimating.

Moreover, since both the reamer (and hence the reamed cavity 52) and the acetabular cup 12 are configured as nearly true hemispheres having similar sizes, the outer surface of the sidewall 26 of the cup 12 contacts the reamed hemispherically-shaped cavity 52 of the acetabulum 16 along substantially all of the surface of the cavity 52. As described above, this feature causes the outer porous surface of the sidewall 26 of the acetabular cup 12 to "scratch" or otherwise slightly abrade substantially all of the wall surface of the cavity 52 as the cup 12 is press fit into the cavity 52. Such slight abrading advantageously facilitates bone ingrowth into the porous outer surface of the acetabular cup 12.

Further, the similar configuration and size of the acetabular cup 12 and the reamed cavity 52 also allows the cup 12 to be fully seated into a position in which the annular rim 30 is substantially flush with the distal surface of the acetabulum 16 (see FIG. 5) without requiring significant amounts of "estimating" by the surgeon during reaming of the bone.

Moreover, use of a reamer that is slightly smaller than the acetabular cup provides preferable amounts of resistance thereby firmly retaining the acetabular cup upon press fit thereof into the cavity without requiring insertion forces large enough to crack or otherwise break the acetabulum.

While the invention has been illustrated and described in detail in the drawings and foregoing description, such an illustration and description is to be considered as exemplary and not restrictive in character, it being understood that only the preferred embodiment has been shown and described and that all changes and modifications that come within the spirit of the invention are desired to be protected.

There is a plurality of advantages of the present invention arising from the various features of the prosthetic hip assembly and associated method described herein. It will be noted that alternative embodiments of the prosthetic hip assembly and associated method of the present invention may not include all of the features described yet still benefit from at least some of the advantages of such features. Those of ordinary skill in the art may readily devise their own implementations of a prosthetic hip assembly and associated method that incorporate one or more of the features of the present invention and fall within the spirit and scope of the present invention as defined by the appended claims.

What is claimed is:

1. A method of securing an acetabular cup to an acetabulum comprising:

reaming a cavity of a first radius of curvature into an acetabulum with a reamer, the reamer including a reamer head having the first radius of curvature; and press fitting an acetabular cup into the reamed cavity, the acetabular cup having a body defining a dome having an apex, an annular rim, and an outer sidewall extending therebetween, wherein said annular rim defines a plane and has a center point lying in said plane, wherein a radial distance between said center point and said sidewall gradually increases from said apex to said annular rim, wherein said radial distance from said center point to said annular rim defines a first given length, 1L, wherein said radial distance from said center point to said apex defines a second given length, 2L, wherein said second given length is less than said first given length, wherein said first given length is greater than said first radius of curvature, and wherein said second given length is approximately equal to said first radius of curvature.

2. The method of claim 1, further comprising:

inserting a liner into the acetabular cup.

3. The method of claim 2, wherein inserting a liner into the acetabular cup includes inserting a liner made of a polymeric material into the acetabular cup.

4. The method of claim 1, wherein $0.5 \text{ mm} \leq 1L-2L \leq 2.0 \text{ mm}$.

5. The method of claim 1, wherein 1L-2L is approximately 1 mm.

6. The method of claim 1, wherein said acetabular cup comprises a titanium alloy.

7. The method of claim 6, wherein said titanium alloy comprises Ti-6Al-4V.

8. The method of claim 1, wherein an outside surface of said body is porous.

9. The method of claim 8, wherein said porous outside surface is configured to enhance bone ingrowth.

10. A method of securing an acetabular cup to an acetabulum comprising:

reaming a cavity of a first radius of curvature into an acetabulum with a reamer, the reamer including a reamer head having the first radius of curvature; and press fitting an acetabular cup into the reamed cavity, the acetabular cup being a dome-shaped and having an apex, an annular rim, and an outer sidewall extending therebetween, wherein said annular rim defines a plane and has a center point lying in said plane, wherein a radial distance between said center point and said sidewall gradually increases from said apex to said annular rim, wherein said radial distance from said center point to said annular rim defines a first given length, 1L, wherein said radial distance from said center point to said apex defines a second given length, 2L, wherein said second given length is less than said first given length, and wherein said first given length is greater than said first radius of curvature.

11. The method of claim 10, wherein $0.5 \text{ mm} \leq 1L-2L \leq 2.0 \text{ mm}$.

12. The method of claim 11, wherein 1L-2L is approximately 1.0 mm.

13. The method of claim 10, wherein said acetabular cup comprises a titanium alloy.

14. The method of claim 13, wherein said titanium alloy comprises Ti-6Al-4V.

15. The method of claim 10, wherein an outside surface of said acetabular cup is porous.

* * * * *